United States Patent [19]

Lewis et al.

[11] Patent Number: 5,068,105

[45] Date of Patent: Nov. 26, 1991

[54] FUNGAL FORMULATION FOR BIOCONTROL OF SOILBORNE PLANT PATHOGENS

[75] Inventors: Jack A. Lewis, Columbia; Douglas Lumsden, Bowie; George Papavizas, Beltsville; Martha D. Hollenbeck, Hyattsville; James F. Walter, Ashton, all of Md.

[73] Assignees: W. R. Grace & Co.-Conn., New York, N.Y.; The United States of America as represented by the Secretary of Agriculture, Washington, D.C.

[21] Appl. No.: 322,445

[22] Filed: Mar. 13, 1989

[51] Int. Cl.$^5$ .................. A61K 35/70; C12N 1/14; A01N 63/04

[52] U.S. Cl. .................. 424/93; 435/254; 435/932; 435/933; 435/945; 47/57.6; 47/DIG. 9

[58] Field of Search .......... 47/57.6, DIG. 9; 435/254, 932, 933, 945; 424/93

[56] References Cited

U.S. PATENT DOCUMENTS

| | | | |
|---|---|---|---|
| 4,061,488 | 12/1977 | Mann | 71/77 |
| 4,259,317 | 3/1981 | Vesely et al. | 424/93 |
| 4,477,433 | 10/1984 | Hultman | 435/254 |
| 4,678,669 | 7/1987 | Ricard | 424/93 |
| 4,713,342 | 12/1987 | Chet et al. | 435/254 |
| 4,724,147 | 2/1988 | Marois et al. | 424/93 |
| 4,774,186 | 9/1988 | Schaefer, Jr. et al. | 435/257 |
| 4,817,333 | 4/1989 | Szepessy et al. | 47/57.6 |
| 4,828,600 | 5/1989 | McCabe et al. | 47/57.6 |

FOREIGN PATENT DOCUMENTS 0242990 1/1987 European Pat. Off.
226394 6/1987 European Pat. Off.
00966 2/1988 PCT Int'l Appl.

OTHER PUBLICATIONS

Liu et al., Biol. Abstracts vol. 70 (1980) 46536.
Bernler et al., Chem. Abstracts vol. 83 (1975), 77128u.
Backman et al., Phytopathology, vol. 65, pp. 819-821, (1975).
Hadar et al., Phytopathology, vol. 69, pp. 64-68 (1979).
Fravel et al., Phytopathology, vol. 75, pp. 774-777 (1985).
Lewis et al., Phytopathology, vol. 75, pp. 812-817 (1985).
Lewis et al., Proc Intern. Contr. Rel. Bioact. Mater., vol. 12, pp. 341-343 (1985).
Paulitz et al., J. Amer. Soc. Hort. Sci., vol. 111, pp. 810-814 (1986).

Primary Examiner—Jacqueline Stone
Attorney, Agent, or Firm—Krafte Jill H.; Vanessa L. Appleby

[57] ABSTRACT

A fungal biocontrol preparation for control or prevention of plant fungal diseases comprises sporulated fungal biomass, a carrier and acid. The carrier preferably is vermiculite. The biocontrol preparation is resistant to bacterial proliferation in storage and handling and is effective in controlling damping-off diseases caused by soilborne fungal pathogens.

25 Claims, No Drawings

FUNGAL FORMULATION FOR BIOCONTROL OF SOILBORNE PLANT PATHOGENS

BACKGROUND OF THE INVENTION

This invention relates generally to the control and prevention of soilborne diseases and to the enhancement of plant health through the use of biological agents. More specifically, an effective and stable dry biomass delivery system for these agents is disclosed. Biocontrol formulations of this invention contain sporulated microbial biomass which, when moistened and added to soil or soilless mix, allows growth of the biocontrol agent through the soil or soilless mix to reduce infestation of soilborne plant pathogens and the diseases these pathogens cause to growing plants.

The use of biological agents for control of plant diseases is not itself a new idea, nor is the controlled release of such agents from a matrix. For example, Lewis et al., "Formulation and Delivery Systems for Biocontrol Agents Effective Against Soilborne Plant Pathogenic Fungi," Proceed. Intern. Symp. Control. Rel. Bioact. Mater., Vol. 12, pp. 341-3 (1985), describes the use of alginate pellets containing propagules of potential fungal and bacterial biocontrol isolates to reduce the incidence of damping-off diseases in cotton, sugar beets and radish seedlings. Similarly, Fravel et al., "Encapsulation of Potential Biocontrol Agents in an Alginate-Clay Matrix," Phytopathology, Vol. 75, pp. 772-7 (1985), discloses a method for the encapsulation in alginate pellets of microorganisms that have potential to control plant diseases.

Backman et al., "A System for the Growth and Delivery of Biological Control Agents to the Soil," Phytopathology, Vol. 65, pp. 819-21 (1975) describes a diatomaceous earth granule impregnated with molasses, disclosed as suitable for growth and delivery of *Trichoderma harzianum*. Paulitz et al., "Effect of Peat:Vermiculite Mixes Containing *Trichoderma harzianum* on Increased Growth Response of Radish," J. Amer. Soc. Hort. Sci., Vol. 111, pp. 810-16 (1986) describes addition of *T. harzianum* to mixes of Canadian sphagnum peat and vermiculite for increased growth of radishes, independent of detectable plant pathogens. European Patent Application No. 86309438.9 (Agracetus), discloses a fungal culture product in which a medium of ground vermiculite, a nutrient and water is prepared and inoculated with a microbial culture.

For purposes of this discussion, the term "mycofungicides" shall mean microbes which act in the control of fungal diseases in plants. Soilborne diseases, caused by about fifty genera of fungi, and a few bacteria and viruses, cause about 50% of the losses due to plant diseases. It is conservatively estimated that, in the United States alone, soilborne diseases cause at least $5 billion losses on crops annually. A major obstacle to the implementation of biological control is a lack of technology in developing and formulating effective and stable preparations which can be produced commercially and which will be accepted in agricultural and horticultural systems.

SUMMARY OF THE INVENTION

The dry delivery system of this invention is very effective for enhancing plant health in consumer, horticultural and agricultural applications. The biocontrol composition comprises a carrier and sporulated fungi. Preferably, the sporulated biomass is rich in chlamydospores. The composition, or its components, is treated with dilute acid to reduce bacterial proliferation.

It is a primary purpose of this invention to provide an economical delivery system for the application of mycofungicides or other biological agents to soils in consumer, horticultural and agricultural settings for prevention of soilborne diseases and for the enhancement of plant health via soilborne biological activity. It is a related objective that the delivery system be easy to handle and apply in these settings.

Another important object is to provide a biomass delivery system which can be formulated and packaged primarily under nonsterile conditions without detrimental bacterial contamination. The delivery system of this invention is easily stored and shipped. It can be stored in compact containers and can be stored for extended periods. The acid treatments of this invention reduce or eliminate bacterial proliferation.

An additional object of the invention is to provide to the industry a dried material which comprises a temporarily inactive form of a biological agent. It is intended that the biological agent can be maintained until the time of application under conditions which would otherwise result in cell death. Upon application to the soil, seed or roots, and with wetting, the inactive agent may be activated, or reconverted into biologically active form. A related object is the provision of a biomass delivery system in which the biocontrol formulation is moistened and activated with dilute acid, enabling it to resist contamination by airborne bacteria.

DETAILED DESCRIPTION OF THE INVENTION

The invention disclosed herein is a delivery system for applying biological mycofungicides or other biologically active agents to soils to control or prevent plant fungal diseases (such as "damping-off" disease) or to provide some beneficial result to the plant. A fungicidally effective amount of the biocontrol preparation is used. The biological plant control composition of this invention comprises a carrier, preferably vermiculite, and fungal biomass. The fungi are selected from species which are effective for control of soilborne diseases or maintenance of plant health. The biological control preparation is prepared for delivery by: (1) growing the selected fungus and allowing it to sporulate under conditions favoring production of resistant spores or other survival structures, (2) blending the biomass with a dilute acid, (3) mixing the biomass with carrier, and (4) drying the mixture. This dried preparation is first activated and then applied to soil or growth medium adjacent to the plants to be protected, or is applied as a seed coating. The spores germinate to produce vegetative cells which act to control the target plant pathogens or to otherwise enhance the health of the plant.

Fungi may reproduce through the formation of sexually or asexually produced spores. Spores produced under unfavorable conditions (e.g., chlamydospores, ascospores, etc.) are quite resistant to hostile environmental conditions, such as heat, dryness, unfavorable pH or nutrient conditions, etc. When favorable conditions return, the spores germinate. Under continued favorable conditions, large numbers of asexually derived spores may be produced. This causes rapid spread of the fungus.

In order for fungal biocontrol to work for soilborne diseases such as those described above, living, actively metabolizing fungi must be present in the vicinity of the plant pathogen. This may be at a distance from the germinating seed or may be on or near the root. Biocontrol of these soilborne plant pathogens requires the presence of the living antagonist fungi where the pathogens exist and/or where they attack the plant. Moreover, the antagonist fungi must be present during the early part of the plant life cycle, which is when the root system is being established and when the plant is most vulnerable to soilborne fungal diseases.

The delivery system described herein meets these requirements. The carrier/biomass composition is versatile enough to be applied in agricultural, horticultural and consumer settings in such a manner that the biocontrol fungi permeate the infested soil. The dried product may be applied on or as a mixture with the soil or soilless mix in which seeds or seedlings are to be planted. It is preferred, however, to mix the biocontrol product with a dilute acid (for example, hydrochloric, acetic or formic acid) for application to the soil as a drench. Alternatively, the product may be mixed with water and applied as a simple aqueous solution. In still another application, the product may be used as a seed coat. In any event, upon wetting of the soil and biocontrol product, the spores begin to germinate in the soil, thereafter acting as biocontrol agents against the target pathogens.

Biologically active fungi are selected and prepared according to the method described herein. A number of fungi are known to control diseases caused by plant pathogenic fungi. Many more have the potential to be effective in reducing the incidence of soilborne disease. Biocontrol fungi which can be used to control damping-off diseases include:

*Trichoderma viride,*
*Trichoderma hamatum,*
*Trichoderma harzianum,*
*Talaromyces flavus,*
*Gliocladium virens,*
*Gliocladium roseum,*
*Paecilomyces fumosoroseus,*
*Penicillium oxalicum,* and
*Laetisaria arvalis.*

For example, *Talaromyces flavus* is used to control *Verticillium wilt* of eggplant which is caused by *Verticillium dahliae.* As other examples, species of *Gliocladium* and *Trichoderma* are effective in reducing the density of the pathogen *Rhizoctonia solani* and *Pythium ultimum* in the soil, which thereby reduces the incidence of cotton and sugar beet damping-off.

For preparation of the product of this invention, the desired biocontrol agent is selected, is grown in culture and is caused to sporulate. Although this description refers to preparation of a single fungus, it will be appreciated that a mixture of genera or species may be desirable in some applications. Cultures of common species of fungi, such as those examples listed above, are readily available from sources such as the Agricultural Research Service Culture Collection at the Northern Regional Research Laboratory (NRRL), 1815N. University Street, Peoria, Ill. 61604 and the American Type Culture Collection (ATCC), 12301 Parklawn Drive, Rockville, Md. 20852, as well as from private, university and government sources.

The fungal culture is maintained on a medium suitable for sustaining growth (i.e., containing carbon and nitrogen sources) under appropriate culture conditions for the species selected. The ability to grow the biological agents used in this invention is within the knowledge and ability of one of ordinary skill in the art. Conventional large-scale liquid fermentors can be used.

Fermentation is continued until sporulation occurs. Sporulation may be induced by continuing to culture to depletion of the nutrients required by the selected biological agent. Alternative methods for induction of sporulation, such as heat or temperature shock, may be used as well. With such biocontrol fungi as Trichoderma and Gliocladium it is preferred to obtain biomass rich in chlamydospores because these spores, rather than the conidia, are the resistant survival structures of the biocontrol fungi. With other fungi, such as Laetisaria, specialized mycelium may form as the resistant structure, and with Talaromyces, ascospores or conidia may form. In other species, blastospores or oospores would be the resistant survival structure.

Liquid fermentation media substrates such as brewer's yeast, molasses, corn steep liquor, corn sugar, etc. are suitable culture media and are readily available. Fermentation is continued until large quantities of resistant spores are produced, that is, at least about $10^6$ CFU per gram dry weight of biomass. The sporulated cell mass is then harvested.

Preferably, the cell mass is concentrated prior to further processing. Concentration eliminates the need for handling the culture medium along with the cell mass, thus streamlining processing requirements as well as concentrating the biocontrol agent. The biomass may be separated from the spent medium by filtration, centrifugation or any other convenient method. The biomass preferably is homogenized or blended while wet or moist, prior to its addition to the vermiculite. Advantageously, this invention allows for formulation directly from the wet biomass, without the need for a mid-stage drying step. Alternatively, the biomass may be dried and powdered, for example by milling or grinding to particles preferably sized to pass through a 40-mesh screen.

The biomass, whether wet or dried, is treated with a dilute acid prior to formulation of the biomass/carrier biocontrol product at a concentration effective to inhibit bacterial proliferation during formulation and upon rewetting of the dried product. The biomass and acid are blended, for example, in a homogenizer. It is preferred that dilute acid is added to moist biomass in relative quantities such that a volume of 200.0 ml is attained for every 115.0 gm biomass (dry weight basis), although biomass equivalent from about 3.0 to about 30.0 gm (dry weight basis) may be used. Dilute acids such as hydrochloric acid, sulfuric acid, nitric acid, formic acid, acetic acid and the like may be used. Acid concentrations in the range of about 0.02N to 0.1N are expected to be suitable. Most preferred is a 0.05N dilution of hydrochloric acid. Treatment with dilute acid is conducted at this stage in order to prevent airborne bacteria from growing on the biomass/carrier combination during drying.

The carrier is a porous material, capable of supporting fungal growth and compatible with the plant environment. Vermiculite, perlite, diatomaceous earth and mineral wool are examples of suitable carriers. Vermiculite is preferred in the preparation of the biocontrol composition of this invention. Commercially available vermiculite (i.e., grade 2) is preferred, but other grades or sizes (i.e., grade 3) may be suitable. The vermiculite most preferably is pretreated to reduce the level of contaminating microorganisms. Preferably, the vermiculite may be heated, i.e., at 80°-90° C. or higher for up to about 48 hours or longer, or it may be irradiated. Microbial decontamination may be accomplished chemically, provided that there is no chemical interference with fungal viability and growth.

Returning to the preferred embodiment, the blended biomass/acid mixture is then added to the vermiculite. By adding pre-formed sporulated biomass to the vermiculite, rather than developing it on the vermiculite, sterile conditions are required only for the biomass culture steps. Sterile facilities are not required for handling the biomass-vermiculite combination. Mixing, handling, measuring and transporting can be done under non-sterile conditions by conventional methods, thus simplifying the preparation and handling procedures.

The biomass/acid mixture is added to the vermiculite in a ratio of about 3:1 to about 1:1. Preferably, about 200.0 ml biomass/acid (equivalent to 15.0 gm dry weight biomass) is used per 100.0 gm vermiculite. The biomass and vermiculite are thoroughly mixed.

This mixed preparation is slowly dried to a total volatiles content of less than about 10.0%, most preferably less than about 2.0%. At low total volatiles levels, both bacterial and fungal growth is minimized or eliminated, allowing storage of the biocontrol preparation. It is preferred that the preparation be as dry as possible to decrease bacterial and fungal growth at this stage. The mixture may, for example, be thinly layered (e.g., up to about 2.0 cm thick) and then air dried. Other convenient methods of drying may be employed. The dried biocontrol preparation is shelf-stable and may be stored for up to six weeks or longer.

The dried fungal product of this invention is an amorphous, free-flowing substance of a fluffy, light, granular nature. The composition is in the form of randomly shaped particles. The particles in grade 2 vermiculite typically are less than about 800.0 microns in diameter, but size will depend on the grade of vermiculite used. The dry preparation has a density of about 0.2 gm/cc$^3$ where grade 2 vermiculite is used. The particles typically are dark in color, with the precise color depending on the characteristics of the fungus.

The dried carrier/biomass preparation should contain fungal spores in sufficient quantity to have a viable spore count of at least about $10^3$ colony forming units (CFU) per gram of the dried carrier/biomass product. A colony forming unit is a measure of the viability of the spore preparation. A useful range is about $10^3$ to about $10^{10}$, preferably about $10^4$ to about $10^6$, CFU per gram. It should be appreciated that the preferred spore count of the dried material will depend on the anticipated dosage used in the soil or soilless mix, or on seeds. A dosage of about 10.0 to about 10,000 grams per square meter of soil is suggested.

The dried biocontrol product may be packaged into any container which is suitable for storage and shipment. Dense packing is possible with the material of this invention. Packaging materials and design should be adequate to maintain the low moisture content of the packaged product for its anticipated shelf life.

As mentioned above, the dried biocontrol material may be applied to and/or mixed with the soil or soilless mix in which plants to be protected by the biocontrol agent will be grown. Alternatively, the dried material may be suspended in water or other liquid and applied to the soil as a drench. In an alternative embodiment, plant seeds may be coated with the dried sporulated biomass product. For example, the seeds may be tumbled with the dried material in the presence of a sticky substance such as methyl cellulose or alginate until coated. It is preferred, however, that the biocontrol preparation be moistened with dilute acid and incubated prior to being added to the soil or soilless mix. This is described in detail below.

The dried carrier/biomass product preferably is mixed with a nutrient base prior to use in soil or soilless mix. Wheat bran is a particularly suitable nutrient base. Alternatively, chitin or cellulose-based substances such as corn cobs, peanut hulls and the like, or a mixture thereof, may be used. The nutrient base is first heated (for example, at 80°-90° C. for 48 hours) or otherwise treated to reduce growth of contaminating microorganisms. The carrier/biomass product then may be mixed with the nutrient base and a dilute acid in any convenient container. Dilute hydrochloric acid (e.g., about 0.05N) is particularly suitable. Alternatively, the other acids listed above may be used in this step. Sufficient quantities of liquid are added to support good fungal growth. A 2:1 ratio of liquid to carrier/biomass is preferred but less liquid may be used if desired. A ratio of at least about 1.3:1 must be used for optimal fungal growth in a two day incubation. After re-wetting, the biocontrol preparation preferably has a total volatiles content of about 50–60%.

The mixture of biocontrol product, nutrient base and dilute acid is incubated at room temperature for sufficient time to allow for visible fungal growth. The fungus grows when the carrier/biomass product is moistened and activated by the dilute acid in the presence of the nutrient or food base. For example, the mixture may be loosely covered and incubated for at least about one day, preferably for about two days. Longer incubation periods are less preferred due to excessive conidia formation, which reduces the amount of actively growing hyphae. The fungal hyphae are the active biocontrol agent propagules necessary to inactivate pathogen propagules.

The moistened, growing biocontrol preparation is broken up and mixed with soil or soilless mix at the desired rate, which is between about 0.1 wt. % and about 10.0 wt. %, preferably about 1.0 to about 5.0 wt. %, most preferably about 1.0 to about 2.0 wt. %. An alternative dosage rate is grams per square foot of soil, in which a dosage of about 10.0 to about 10,000 grams/square meter is suggested.

The present invention allows for activation of the fungal spores on the carrier so that the carrier/biomass formulation, when added to soil or soilless mix, permits growth and development of the biocontrol agent under natural conditions. After addition to soil or soilless mix, the effectiveness of the formulation is ascertained by reduction in pathogen inoculum density and in prevention or reduction of soilborne disease. Use of the biocontrol preparations of this invention can reduce or prevent damping-off diseases caused by *Rhizoctonia solani, Pythium ultimum, Sclerotium rolfsii, Verticillium dahliae*, and other species of plant pathogenic fungi.

The examples which follow are given for illustrative purposes and are not meant to limit the invention described herein. The following abbreviations have been used throughout in describing the invention:

°C.—degree(s) Centigrade
CFU—colony forming unit(s)
cc—cubic centimeter
cm—centimeter
gm—gram(s)

M—molar
mg—milligram(s)
ml—milliliter(s)
N—normal
%—percent
TV—total volatiles
wt.—weight

EXAMPLE I

Preparation of Biocontrol Products

Fungal biomass was produced for experimental biocontrol preparations by growth of fungal biocontrol isolates during liquid fermentation of molasses-brewer's yeast medium for a period of 6–10 days, until significant sporulation occurred. Biocontrol formulations were prepared using the following isolates:

| | | |
|---|---|---|
| Gliocladium virens: | Gl-3 | |
| | Gl-21 | |
| Trichoderma hamatum: | TRI-4 | |
| | 31-3 | |
| Trichoderma harzianum: | Th-23-R9 | |
| | Th-87 | |
| Trichoderma pseudokoningii: | 30903 | |
| Trichoderma viride: | TS-1-R3 | |

The cultured biomass was separated from the spent liquid medium through cheesecloth. Each fungal biomass preparation was divided in half, with one half air dried in a fume hood and powdered in a mill to pass a 40 mesh screen, and the other half used moist after the dry weight equivalent was determined on a sample. Both portions were comminuted in a blender with 80.0 ml 0.05N HCl.

A granular preparation of 50.0 gm commercial fine vermiculite (grade 2) was dried at 80°–90° C. for 48 hours, and then mixed with 10.0 gm dry weight equivalent of fungal biomass from the "dried preparation" described above. An equal amount of dried vermiculite was mixed with 10.0 gm dry weight equivalent of fungal biomass from the "moist preparation" described above. Each mixture then was allowed to air dry for 24 hours.

EXAMPLE II

The preparations of Example I were assayed over a six-week period to determine the effect of storage on the viability of the fungi. Serial dilutions of the dry preparations, comminuted in sterile water, were placed on a semi-selective medium containing nutrient and antibiotics (see Papavizas and Lumsden, Plant Disease, 66:1019–1020 (1982)). After one week of incubation, colony-forming-units/gram of dry preparation were determined. This was repeated each week with the stored dry preparations. The results of the "moist preparation" are shown in Table I. Comparable results were obtained from both preparations.

TABLE I

| | CFU/gm Dry Prep. ($\times 10^5$) | |
|---|---|---|
| Storage | Gl-21 | TRI-4 |
| 1 week | 9.6 a$^z$ | 11.5 a |
| 3 weeks | 9.8 a | 7.8 ab |
| 6 weeks | 9.6 a | 5.6 a |

$^z$Duncan's multiple range test (DMRT), $P = 0.05$.

EXAMPLE III

The ability of Gliocladium virens (Gl-21) to grow out from vermiculite/biomass preparations into soil was assessed. Samples of the "dry" Gl-21 vermiculite/biomass preparation of Example I were moistened with 0.05N HCl at the time of addition to soil, and at one day and two days before addition to soil, at an addition rate of 1.0%. Serial dilutions and plating were done as in Example II. Gl-21 populations (CFU) were determined after one and three weeks. The fungus proliferated in soil from all three moistened vermiculite/biomass preparations. After one week of incubation in soil, the population was greater with a two-day moistened preparation than with the other preparations. After three weeks of incubation, all populations were comparable. The results are shown in Table II.

TABLE II

| Pre-Treatment | CFU/gm Soil ($\times 10^8$) | |
|---|---|---|
| Incubation | 1 week | 3 weeks |
| None | 2.0 b$^z$ | 0.1 a |
| 1 Day | 12.3 b | 1.1 a |
| 2 Days | 71.0 a | 1.1 a |

$^z$DMRT, $P = 0.05$.

EXAMPLE IV

The ability of Gliocladium virens (Gl-21) to grow from moistened preparations into soil and reduce survival and saprophytic growth of the soilborne pathogen Rhizoctonia solani (R-23) was determined following the procedure of Example III. Before moistened preparations were added to soil, tablebeet seed infested with R. solani (R-23) was mixed with soil at a rate of 1.0%. Three weeks after seed and the Gl-21 preparation of Example I were incubated in soil, beet seed was retrieved and pathogen survival and saprophytic activity were determined by established procedures (see Lewis and Papavizas, Soil Biology and Biochemistry 19:195–201 (1987)). The results are shown in Table III. The survival data indicate that regardless of how long the acid-moistened preparations were incubated before they were added to the soil, the Gl-21 preparation of this invention significantly reduced pathogen survival. The saprophytic growth data indicates the reduction in inoculum density of the pathogen. All three Gl-21 treatments significantly survival of R. solani. However, only the treatment in which the preparation was moistened at the time of addition to soil reduced saprophytic activity of the pathogen compared to the appropriate control.

TABLE III

| Pre-Treatment Incubation | Gl-21 | Survival of R-23 (%) | Saprophytic Growth of R-23 (%) |
|---|---|---|---|
| None | — | 91.0 a$^z$ | 81.0 a |
| None | + | 71.0 bc | 39.0 bc |
| 1 Day | — | 91.0 a | 49.0 b |
| 1 Day | + | 63.0 c | 35.0 bc |
| 2 Days | — | 86.0 ab | 47.0 bc |
| 2 Days | + | 58.0 c | 31.0 c |

$^z$DMRT, $P = 0.05$.

EXAMPLE V

The ability of Trichoderma and Gliocladium virens to grow out from two-day-old moistened vermiculite/biomass preparations, proliferate in soil and reduce survival and saprophytic growth of Rhizoctonia solani (R-23) was determined as in Example III and IV. The results are shown in Table IV. Biocontrol formulations were prepared as in Example I. Isolates varied in their ability to proliferate from the moistened vermiculite/biomass preparations, but all developed greater than $10^7$ CFU/gm of soil. All isolates tested, except Th-23-R9, reduced R. solani survival in beet seed; the most effective isolates were Th-87 and TRI-4. Two (TS-1-R3, TRI-4) of the eight isolates prevented saprophytic growth of the pathogen in soil.

TABLE IV

| Biocontrol Formulation | Biocontrol Population (CFU × 10^6/ gm soil) | Survival of R-23 (%) | Saprophytic Growth of R-23 (%) |
|---|---|---|---|
| Control (R-23) | — | 92.0 a | 70.0 bcd |
| Control (R-23/vermic.) | — | 96.0 a | 94.0 a |
| T. viride TS-1-R3 | 74.0 c[z] | 31.0 c | 40.0 e |
| T. pseudokoningii 30903 | 20.0 e | 65.0 b | 85.0 abc |
| T. harzianum | | | |
| Th-23-R9 | 150.0 a | 86.0 a | 97.0 a |
| Th-87 | 98.0 b | 6.0 d | 66.0 cd |
| T. hamatum | | | |
| 31-3 | 26.0 de | 35.0 c | 100.0 a |
| TRI-4 | 34.0 de | 4.0 d | 7.0 f |
| G. virens | | | |
| Gl-3 | 72.0 c | 32.0 c | 90.0 ab |
| Gl-21 | 43.0 d | 28.0 c | 55.0 de |

[z]DMRT, $\underline{P}$ = 0.05.

EXAMPLE VI

The biocontrol capability of vermiculite/biomass preparations of Trichoderma hamatum (TRI-4), Trichoderma harzianum (Th-87) and Gliocladium virens (Gl-21) to prevent cotton damping-off caused by the pathogen Rhizoctonia solani (R-23) was established in greenhouse studies. The vermiculite/biomass preparations of Example I were used. The preparations were moistened and incubated for two days. A sufficient amount of each preparation to provide biocontrol addition rates of 0.5 and 2.0% was mixed with a loamy sand to which was added a millet inoculum of R-23 at a rate of 0.02%. After one week of incubation, soils were planted to benomyl-treated cotton seed (Stoneville 213), and pots were maintained by conventional procedures. Plant stand was determined after three weeks of growth. The results using the "moist preparation" of Example I are shown in Table V. All biocontrol preparations significantly prevented cotton damping-off. Stands were comparable to, or better than, those in non-infested soil. Treatment of soil with a moistened preparation at a rate of 0.5% was as effective as a 2.0% rate.

TABLE V

| Biocontrol Formulation | Dosage Add'n (%) | Cotton Stand (% at 3 wks) | |
|---|---|---|---|
| | | Exper. 1 | Exper. 2 |
| Control (no R-23) | — | 51.0 b[z] | 72.0 a |
| Control (R-23) | — | 1.0 c | 38.0 b |
| Control (R-23/vermic) | — | 4.0 c | 27.0 b |
| TRI-4 | 0.5 | — | 61.0 a |
| TRI-4 | 2.0 | 75.0 a | 74.0 a |
| Th-87 | 0.5 | — | 73.0 a |
| Th-87 | 2.0 | 50.0 b | 66.0 a |
| Gl-21 | 0.5 | — | 60.0 a |
| Gl-21 | 2.0 | 75.0 a | 64.0 a |

[z]DMRT, $\underline{P}$ = 0.05.

EXAMPLE VII

The biocontrol capability of vermiculite/biomass preparations of the formulations used in Example VI for prevention of damping-off of zinnia in REDI-EARTH® soilless mix (W. R. Grace & Co.-Conn.) caused by Rhizoctonia solani (R-23) and Pythium ultimum was determined in the greenhouse. Freshly moistened and two-day incubated moistened vermiculite/biomass preparations of each formulation ("moist" and "dry") were added at a rate of 1.0% dry weight equivalent to REDI-EARTH soilless mix individually infested with pathogens. After one week of incubation, soils were planted to zinnia seed and routinely maintained. Healthy plant stand (percent of control) was determined after four weeks of growth. These results are shown in Table VI. Dry and moist preparations of Gl-21 and moist preparations of TRI-4 and Th-87 prevented Rhizoctonia damping-off of zinnia, but none of the tested preparation was effective in preventing Pythium damping-off of zinnia.

TABLE VI

| Biocontrol Formulation | Type of Prep. | Zinnia Stand (% at 4 wks) | |
|---|---|---|---|
| | | R. solani | P. ultimum |
| Control | — | 21.0 d[z] | 9.0 ab |
| Control (vermic.) | dry | 21.0 d | 9.0 ab |
| TRI-4 | dry | 25.0 d | 6.0 b |
| Th-87 | dry | 35.0 cd | 8.0 ab |
| Gl-21 | dry | 72.0 a | 12.0 ab |
| Control (vermic.) | moist | 23.0 d | 17.0 a |
| TRI-4 | moist | 51.0 bc | 14.0 ab |
| Th-87 | moist | 47.0 c | 11.0 ab |
| Gl-21 | moist | 65.0 ab | 14.0 ab |

[z]DMRT, $\underline{P}$ = 0.05.

EXAMPLE VIII

The biocontrol capability of preparations of the formulations used in Example VI to prevent damping-off of beans in a compost soil caused by the soilborne pathogen Sclerotium rolfsii was determined in the greenhouse. Soils, infested with sclerotia of S. rolfsii (Sr-1), were mixed with two-day incubated moistened vermiculite/biomass preparations at a rate of 0.5% (dry weight equivalent) and were incubated for one week. At this time, soils were planted to beans (Topcrop) and routinely maintained. Plant stand was determined after one and three weeks of growth. These results are shown in Table VII. All preparations significantly prevented bean damping off. TRI-4 was more effective than Th-87 or Gl-21 and, after one week, allowed a stand comparable to that in the non-infested control.

TABLE VII

| Biocontrol Formulation | Bean Stand (%) | |
|---|---|---|
| | 1 week | 3 weeks |
| Control (no Sr-1) | 98.0 a[z] | 98.0 a |
| Control (Sr-1) | 0.0 c | 0.0 d |
| Control (Sr-1/vermic.) | 6.0 c | 0.0 d |
| TRI-4 | 90.0 a | 78.0 b |
| Th-87 | 60.0 b | 22.0 c |
| Gl-21 | 58.0 b | 24.0 c |

[z]DMRT, $\underline{P}$ = 0.05.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

We claim:

1. A biocontrol preparation for control or prevention of plant fungal diseases which is a mixture of a porous carrier and sporulated biomass of one or more species of fungus effective for control of soilborne plant diseases, said biomass having been grown under liquid fermentation conditions, separated from the fermentation medium, treated with a dilute acid to reduce bacterial contamination, and dried to temporarily inactivate and stabilize the mixture, said biomass/carrier mixture subsequently having been moistened and activated by incubation with dilute acid and a nutrient base for a sufficient time to allow for visible fungal growth prior to applying to soil or growth medium.

2. The biocontrol preparation of claim 1 in which said sporulated biomass comprises chlamydospores, ascospores, specialized mycelium, blastospores or oospores.

3. The biocontrol preparation of claim 1 which comprises a fungicidally effective amount of said fungus for controlling soilborne fungal pathogens.

4. The biocontrol preparation of claim 3 which has a viable spore count of at least $10^3$ colony forming units of said fungus per gram (dry weight).

5. The biocontrol preparation of claim 1 in which said fungi are *Trichoderma viride, Trichoderma hamatum, Trichoderma harzianum, Talaromyces flavus, Gliocladium virens, Gliocladium roseum, Paecilomyces fumosoroseus, Penicillium oxalicum* or *Laetisaria arvalis*.

6. The biocontrol preparation of claim 1 in which said porous carrier is vermiculite, perlite, diatomaceous earth, mineral wool or a mixture thereof.

7. The biocontrol preparation of claim 1 which is a dried, free-flowing substance in its inactivated form.

8. The inactivated biocontrol preparation of claim 7 which has a total volatiles content of less than about 10.0%.

9. The inactivated biocontrol preparation of claim 8 which has a total volatiles content of less than about 2.0%.

10. The biocontrol preparation of claim 1 in which said nutrient base is wheat bran, chitin, corn cobs, peanut hulls or a mixture thereof.

11. The biocontrol preparation of claim 1 which further comprises dilute acid and which has a total volatiles content of about 50 to about 60% in its activated form.

12. The activated biocontrol preparation of claim 11 in which said acid is hydrochloric acid, sulfuric acid, nitric acid, formic acid, acetic acid or mixtures thereof.

13. The activated biocontrol preparation of claim 11 in which said acid is 0.05N hydrochloric acid.

14. A composition useful for the enhancement of plant health consisting of plant seeds coated with a biocontrol preparation which is a mixture of a sporulated biomass of one or more species of fungus effective for control of soilborne plant disease and a porous carrier, said biomass having been grown under liquid fermentation conditions, separate from the fermentation medium, treated with a dilute acid in order to inhibit bacterial proliferation, and dried to temporarily inactivate and stabilize the mixture.

15. The composition of claim 14 in which said porous carrier is vermiculite, perlite, diatomaceous earth, mineral wool or a mixture thereof.

16. A method of enhancing plant health by applying to the soil or growth medium adjacent to said plant a biocontrol preparation for control or prevention of plant fungal diseases, said biocontrol preparation comprising sporulated biomass of one or more species of fungus effective for control of soilborne plant disease and a porous carrier, said biomass having been grown under liquid fermentation conditions, separated from the fermentation medium, treated with a dilute acid in order to inhibit bacterial proliferation, and dried to temporarily inactivate and stabilize the mixture, said biomass/carrier mixture having been subsequently moistened and activated by incubation with dilute acid and a nutrient base for a sufficient time to allow for visible fungal growth prior to applying to the soil or growth medium.

17. The method of claim 16 in which said porous carrier is vermiculite, perlite, diatomaceous earth, mineral wool or a mixture thereof.

18. The method of claim 16 in which said dilute acid is added to activate the mixture and to bring the total volatiles content of the biocontrol preparation to about 50 to 60%.

19. The method of claim 16 in which said acid is hydrochloric acid, sulfuric acid, nitric acid, formic acid, acetic acid or a mixture thereof.

20. The method of claim 19 in which said acid is 0.05N hydrochloric acid.

21. The method of claim 16 in which said moistened biocontrol preparation is incubated up to about two days prior to applying to said soil or growth medium.

22. The method of claim 16 in which said biocontrol preparation is applied to the soil or growth medium at a rate of between about 0.1 and about 10.0 weight percent.

23. The method of claim 22 in which said rate is between about 1.0 and about 2.0 weight percent.

24. The method of claim 16 in which said biocontrol preparation is applied to the soil or growth medium at a rate of between about 10.0 and about 10,000 grams per square meter.

25. A method for preparing a biocontrol preparation for control of prevention of plant fungal diseases comprising
   (a) fermenting one or more species of fungus effective for control of soilborne plant diseases in a liquid culture medium until sporulation occurs and resistant spores are produced,
   (b) harvesting the sporulated biomass,
   (c) concentrating the sporulated biomass to separate it from said culture medium,
   (d) treating said biomass with dilute acid at a concentration effective to inhibit bacterial proliferation,
   (e) mixing the biomass/acid mixture of step (d) with a porous carrier,
   (f) drying the carrier/biomass/acid mixture to form a mixture wherein the biomass is inactive and stable indefinitely,
   (g) activating the mixture of step (f) by addition of dilute acid to yield actively-growing mycelium of the biocontrol fungus.

* * * * *

UNITED STATES PATENT AND TRADEMARK OFFICE
CERTIFICATE OF CORRECTION

PATENT NO. : 5,068,105

DATED : November 26, 1991

INVENTOR(S) : J. A. Lewis, R. D. Lumsden, G. C. Papavizas, M. D. Hollenbeck, J. F. Walter It is certified that error appears in the above-identified patent and that said Letters Patent is hereby corrected as shown below:

Column 4, line 47: "115.0 gm" should be --15.0 gm--.

Claim 14, col. 11, line 62: "separate" should be --separated--.

Signed and Sealed this

Sixteenth Day of March, 1993

Attest:

STEPHEN G. KUNIN

*Attesting Officer*     Acting Commissioner of Patents and Trademarks